United States Patent [19]

Shutske et al.

[11] Patent Number: 4,927,820
[45] Date of Patent: May 22, 1990

[54] FUSED HETEROCYCLIC DERIVATIVES OF 1,2,3,4-TETRAHYDROACRIDINE

[75] Inventors: Gregory M. Shutske, Somerset; Kevin J. Kapples, Little York, both of N.J.

[73] Assignee: Hoechst Roussel Pharmaceuticals Inc., Somerville, N.J.

[21] Appl. No.: 276,259

[22] Filed: Nov. 25, 1988

[51] Int. Cl.$^5$ .......................................... C07D 498/00
[52] U.S. Cl. ................................. 514/229.5; 544/91; 544/248
[58] Field of Search ................ 544/248, 91; 514/225, 514/229.8, 257, 286, 229.5

[56] References Cited

U.S. PATENT DOCUMENTS 4,695,573  9/1987  Shutske et al. ................. 514/290

FOREIGN PATENT DOCUMENTS 8902739  4/1989  World Int. Prop. O. .
8902740  4/1989  World Int. Prop. O. .

OTHER PUBLICATIONS

Chalody, et al., "Tetrahedron Letters", 28(42), 1987, 5029-32.

Primary Examiner—Mukund J. Shah
Assistant Examiner—E. C. Ward
Attorney, Agent, or Firm—Tatsuya Ikeda

[57] ABSTRACT

There are disclosed compounds having the formula

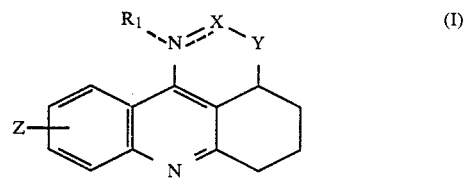

where
- $R_1$ is hydrogen, loweralkyl or arylloweralkyl;
- Z is hydrogen, loweralkyl, loweralkoxy, halogen, hydroxy, nitro or trifluoromethyl;
- Y is O or $NR_2$, $R_2$ being hydrogen, loweralkyl or arylloweralkyl; and
- X is $CR_3$, $CHR_3$, C=O, C=S or $CHN(CH_3)_2$, $R_3$ being hydrogen, loweralkyl or aryl;

stereo isomers thereof and pharmaceutically acceptable acid addition salts thereof, which are useful for the treatment of various memory dysfunctions characterized by decreased cholinergic function, such as Alzheimer's disease.

13 Claims, No Drawings

FUSED HETEROCYCLIC DERIVATIVES OF 1,2,3,4-TETRAHYDROACRIDINE

This invention relates to compounds having the formula

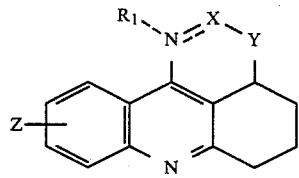

where
R$_1$ is hydrogen, loweralkyl or arylloweralkyl;
Z is hydrogen, loweralkyl, loweralkoxy, halogen, hydroxy, nitro or trifluoromethyl;
Y is O or NR$_2$, R$_2$ being hydrogen, loweralkyl or arylloweralkyl; and
X is CR$_3$, CHR$_3$, C=O, C=S or CHN(CH$_3$)$_2$, R$_3$ being hydrogen, loweralkyl or aryl;
stereo isomers thereof and pharmaceutically acceptable acid addition salts thereof, which are useful for the treatment of various memory dysfunctions characterized by decreased cholinergic function, such as Alzheimer's disease.

Throughout the specification and the appended claims, a given chemical formula or name shall encompass all stereo, geometrical and optical isomers thereof where such isomers exist, as well as pharmaceutically acceptable acid addition salts thereof and solvents thereof such as for instance hydrates.

The two dotted lines appearing in Formula (I) signify that when the linkage between the nitrogen and X is a double bond, the group R$_1$ is absent, whereas when said linkage is a single bond, the group R$_1$ is linked to the nitrogen atom via a single bond. In the former case, the group X is CR$_3$, whereas in the latter case, the group X is CHR$_3$, C=O, C=S or CHN(CH$_3$)$_2$.

The following definitions shall apply throughout the specification and the appended claims.

Unless otherwise stated or indicated, the term loweralkyl denotes a straight or branched alkyl group having from 1 to 6 carbon atoms. Examples of said loweralkyl include methyl, ethyl, n-propyl, iso-butyl, pentyl and hexyl.

Unless otherwise stated or indicated, the term cycloalkyl denotes an alicyclic hydrocarbon group containing 3 to 7 carbon atoms. Examples of said cycloalkyl include cyclopropyl, cyclohexyl and cycloheptyl.

Unless otherwise stated or indicated, the term halogen shall mean fluorine, chlorine, bromine or iodine.

Unless otherwise stated or indicated, the term aryl shall mean an unsubstituted phenyl group or a phenyl group substituted with 1, 2 or 3 substituents each of which being independently loweralkyl, loweralkoxy, halogen, hydroxy or trifluoromethyl.

The compounds of this invention are prepared by utilizing one or more of the steps described below.

Throughout the description of the synthetic steps, the definitions of X, Y, Z, R$_1$, R$_2$ and R$_3$ as given above unless otherwise stated or indicated.

STEP A

A compound of Formula II is reacted with 1,3-cyclohexanedione to afford a compound of Formula III. Typically, said reaction is conducted in a suitable solvent such as benzene or toluene at a temperature of about 50°–150° C.

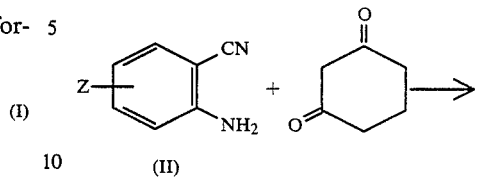

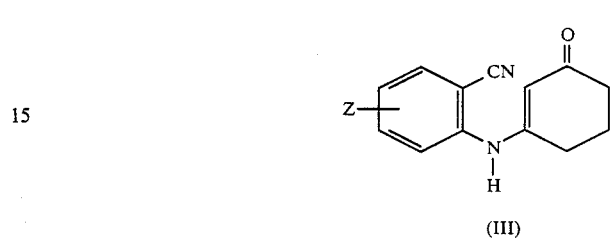

STEP B

A compound of Formula IV is prepared by cyclizing compound III in the presence of a metallic halide such as cuprous chloride, cuprous bromide or cuprous iodide or the like used as a catalyst. Typically said cyclization reaction is conducted in a suitable solvent such as an ethereal solvent including tetrahydrofuran, diethyl ether and dioxane and in the presence of a catalyst and a basic inorganic salt such as potassium carbonate, potassium bicarbonate, sodium carbonate, sodium bicarbonate or the like, at a temperature of about 30°–100° C.

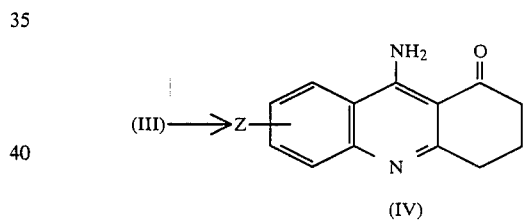

STEP C

A compound of Formula V is prepared by reacting compound IV with a suitable metal hydride such as LiAlH$_4$ in a suitable solvent such as an ethereal solvent including tetrahydrofuran, diethyl ether, dioxane and mixtures thereof at a temperature of from about −20° to about 20° C., and thereafter hydrolyzing the product.

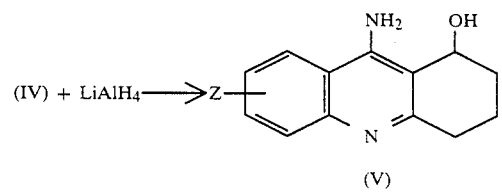

STEP D

A compound of Formula VII is prepared by reacting compound V with an amine of Formula VI in a suitable medium, for instance, an aromatic hydrocarbon such as toluene and preferably in the presence of a suitable catalyst such as p-toluenesulfonic acid. Typically the

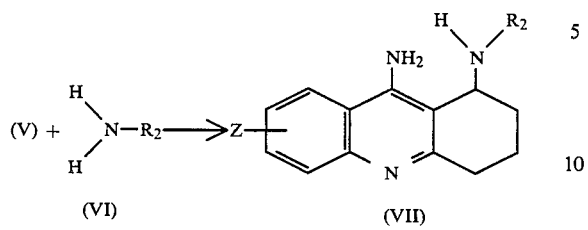
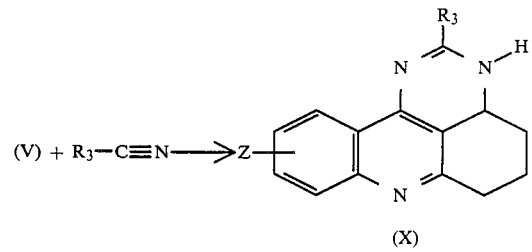

STEP E

Compound IV is allowed to react with a compound of the formula $R_1W$, W being Cl, Br, I or $OSO_2CH_3$, to afford a compound of Formula VIII. Typically, said reaction is conducted in a biphasic system comprising a suitable organic solvent such as dichloromethane, chloroform, benzene, toluene or the like, a strongly alkaline aqueous phase such as 50% aqueous NaOH or the like, the starting compounds and a phase transfer catalyst such as tetrabutylammonium hydrogensulfate at a temperature of about 0°-50° C.

STEP H

Compound IXa (wherein $R_1$ can be hydrogen as well as loweralkyl or arylloweralkyl) is allowed to react with an aldehyde of the formula $$R_3-\overset{\overset{O}{\|}}{C}-H$$

in the presence of morpholine and a suitable solvent including aromatic hydrocarbon such as toluene to afford a compound of Formula XI. Typically, this reaction is conducted at a temperature of 100° to 150° C.

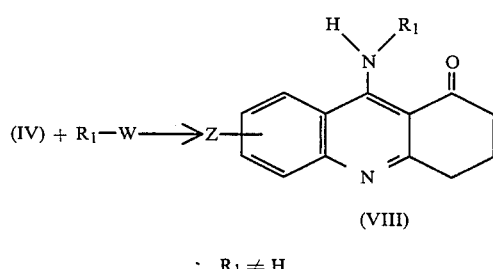
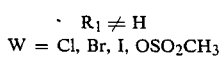

$R_1 \neq H$
$W = Cl, Br, I, OSO_2CH_3$

STEP F

A compound of Formula IX is prepared by reacting Compound VIII with a suitable metal hydride such as $LiAlH_4$ in a suitable solvent such as tetrahydrofuran, diethyl ether, or dioxane at a temperature of from $-20°$ to 20° C. and thereafter hydrolyzing the product.

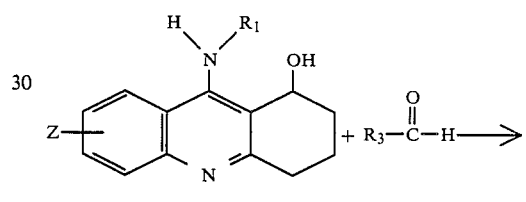

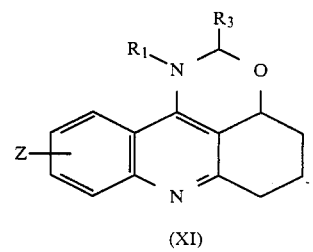

STEP I

Compound IXa is allowed to react with carbonyl diimidazole in a routine manner known to the art to afford a compound of Formula XII. Typically this reaction is conducted in a suitable solvent such as tetrahydrofuran or benzene at a temperature of about 25° to 100° C.

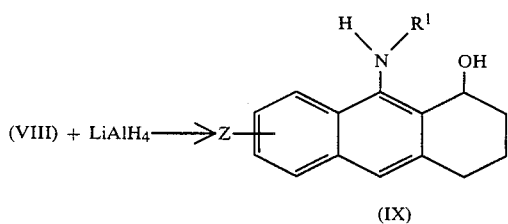

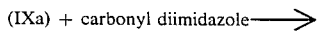

(IXa) + carbonyl diimidazole ⟶

$R_1 \neq H$

STEP G

Compound V is allowed to react with a nitrile compound of the Formula $R_3-C\equiv N$ in a suitable acidic medium such as $CF_3COOH$ containing a low concentration of sulfuric acid to afford a compound of Formula X. Typically, this reaction is conducted at a temperature of 0° to 50° C.

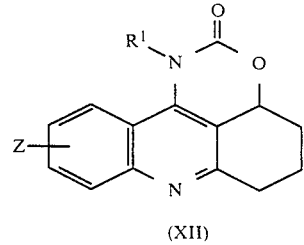

STEP J

Compound IXa is allowed to react with thiocarbonyl diimidazole in a routine manner known to the art to afford a compound of Formula XIII. Typically this reaction is conducted in a suitable solvent such as tetrahydrofuran or benzene at a temperature of about 25° to 100° C.

(IXa) + thiocarbonyl diimidazole ⟶

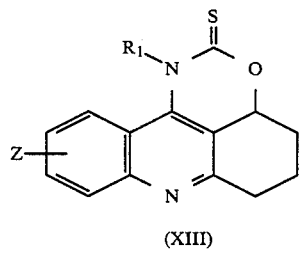

(XIII)

STEP K

Compound IXa is allowed to react with $(CH_3O)_2CHN(CH_3)_2$ in a routine manner known to the art to afford a compound of Formula XIV. Typically this reaction is conducted in a suitable solvent such as methylene chloride, benzene, acetonitrile or N,N-dimethylformamide at a temperature of about 25° to 150° C.

(IXa) + $(CH_3O)_2CHN(CH_3)_2$ ⟶

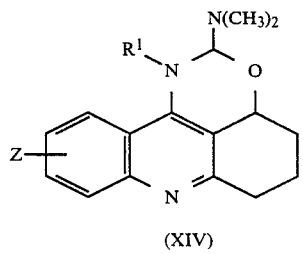

(XIV)

The compounds of Formula (I) of the present invention can be used for the treatment of various memory dysfunctions characterized by decreased cholinergic functions, such as Alzheimer's disease.

This utility can be ascertained by determining the ability of these compounds to inhibit the activity of the enzyme acetylcholinesterase and thereby increase the acetylcholine levels in the brain.

CHOLINESTERASE INHIBITION ASSAY

The ability to inhibit acetylchlinesterase was determined by the photometric method of Ellman et al., Biochem. Pharmacol. 7, 88 (1961). Results of some of the compounds of this invention are presented in Table 1 below along with those of some reference compounds.

TABLE 1

| Compound | Cholinesterase Inhibition $IC_{50}$ (molar conc.) |
|---|---|
| 2-Phenyl-1,2,3a,4,5,6-hexahydro[1,3]-oxazino[6,5,4-kl]acridine | $3.6 \times 10^{-5}$ |

TABLE 1-continued

| Compound | Cholinesterase Inhibition $IC_{50}$ (molar conc.) |
|---|---|
| 2-(4-Fluorophenyl)-1,2,3a,4,5,6-hexahydro-[1,3]oxazino[6,5,4-kl]acridine (Reference Compounds) | $2.1 \times 10^{-5}$ |
| 9-Amino-1,2,3,4-tetrahydroacridine | $3.1 \times 10^{-7}$ |
| Physostigmine | $6.0 \times 10^{-9}$ |

This utility can also be ascertained by determining the ability of these compounds to restore cholinergically deficient memory in the Dark Avoidance Assay. In this assay mice are tested for their ability to remember an unpleasant stimulus for a period of 24 hours. A mouse is placed in a chamber that contains a dark compartment; a strong incadescent light drives it to the dark compartment, where an electric shock is administered through metal plates on the floor. The animal is removed from the testing apparatus and tested again, 24 hours later, for the ability to remember the electric shock.

If scopolamine, an anticholinergic that is known to cause memory impairment, is administered before an animal's initial exposure to the test chamber, the animal re-enters the dark compartment shortly after being placed in the test chamber 24 hours later. This effect of scopolamine is blocked by an active test compound, resulting in a greater interval before re-entry into the dark compartment.

The results for an active compound are expressed as the percent of a group of animals in which the effect of scopolamine is blocked, as manifested by an increased interval between being placed in the test chamber and re-entering the dark compartment. Results of Dark Avoidance Assay for representative compounds of this invention and a reference compound are presented in Table 2.

TABLE 2

| Compound | Dark Avoidance Assay Dose mg/kg body weight | % of animals with scopolamine induced memory deficit reversal |
|---|---|---|
| 2-Phenyl-1,2,3a,4,5,6-hexahydro [2,3]-oxazino[6,5,4-kl]acridine | 5.0 | 27% |
| Physostigmine (Reference) | 0.31 | 20% |

Effective quantities of the compounds of the invention may be administered to a patient by any of the various methods, for example, orally as in capsule or tablets, parenterally in the form of sterile solutions or suspensions, and in some cases intravenously in the form of sterile solutions. The free base final products, while effective themselves, may be formulated and administered in the form of their pharmaceutically acceptable acid addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric and oxalic acids.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compounds, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0–300 milligrams of active compound.

The tablets, pills, capsules, troches and the like may also contain the following ingredients: a binder such as micro-crystalline cellulose, gum tragacanth or gelatin; an excipient such as starch or lactose, a disintegrating agent such as alginic acid, Primogel, cornstarch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent and certain preservatives, dyes, coloring and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of active compound, but may be varied between 0.5 and about 30% of the weight thereof. The amount of active compound in such compositions is such that a suitable dosage will be obtained. Preferred compositions and preparations according to the present inventions are prepared so that a parenteral dosage unit contains between 0.5 to 100 milligrams of active compound.

Examples of the compounds of this invention include:
3a,4,5,6-tetrahydro-2-methyl-(3H)-pyrimidino[4,5,6-kl]acridine;
3a,4,5,6-tetrahydro-2-phenyl-(3H)-pyrimidino[4,5,6-kl]acridine;
2-phenyl-1,2,3a,4,5,6-hexahydro[1,3]oxazino[6,5,4-kl]acridine; and
2-(4-fluorophenyl)-1,2,3a,4,5,6-hexahydro[1,3]oxazino[6,5,4-kl]acridine The following examples are presented in order to illustrate this invention.

EXAMPLE 1

3a,4,5,6-Tetrahydro-2-methyl-(3H)-pyrimidino[4,5,6-kl]acridine, maleate

To a mixture of 9-amino-1,2,3,4-tetrahydroacridin-1-ol (15.3 g) and acetonitrile (7.5 ml) was added 200 ml of a 5% $H_2SO_4/CF_3CO_2H$ solution. The reaction mixture was stirred for one hour, quenched into an iced NaOH solution and extracted with ethyl acetate (10×). The organics were then washed with water and dried (saturated NaCl, $MgSO_4$).

The compound was purified via flash chromatography (5% $Et_3N$/EtOAc) to give 8.4 g of a yellow solid, m.p. 206°–217° C. A 3.2 g portion was dissolved in isopropanol and treated with maleic acid. The resulting solid was filtered and recrystallized from methanol/diethyl ether to give 2.87 g of a white powder, m.p. 207°–207.5° C.

| ANALYSIS: | | | |
|---|---|---|---|
| Calculated for $C_{15}H_{15}N_3 \cdot C_4H_4O_4$: | 64.58% C | 5.42% H | 11.89% N |
| Found: | 64.64% C | 5.41% H | 11.89% N |

EXAMPLE 2

3a,4,5,6-Tetrahydro-2-phenyl-(3H)-pyrimidino[4,5,6-kl]acridine, maleate

To a mixture of 9-amino-1,2,3,4-tetrahydroacridine-1-ol (7.07 g) and benzonitrile (6.75 ml) was added 100 ml of a 5% $H_2SO_4/CF_3CO_2H$ solution. The mixture was stirred to solution and then added to an iced NaOH solution. The precipitate was filtered, dried and purified via flash chromatography (4% $Et_3N$/EtOAc) to give 5.2 g of a yellow solid, m.p. 205°–225° C. A 3.9 g portion was recrystallized from dichloromethane/hexane to give 2.8 g of a yellow solid which was dissolved in isopropanol and treated with a maleic acid solution (in isopropanol) to give 3.4 g of a bright yellow solid, m.p. 230°–231° C. (dec.).

| ANALYSIS: | | | |
|---|---|---|---|
| Calculated for $C_{20}H_{17}N_3 \cdot C_4H_4O_4$: | 69.38% C | 5.10% H | 10.11% N |
| Found: | 69.28% C | 5.00% H | 10.09% N |

EXAMPLE 3

2-Phenyl-1,2,3a,4,5,6-hexahydro[1,3]oxazino[6,5,4-kl]acridine

9-Amino-1,2,3,4-tetrahydroacridine-1-ol (15.0 g) was refluxed in 1 liter of toluene that contained 12.28 g of morpholine and 9.29 g of benzaldehyde that had been freshly washed with $K_2CO_3$. The reaction mixture was refluxed overnight and allowed to cool. The crude product was then filtered off and purified by flash chromatography (20% isopropanol/ethyl acetate) to give 8.07 g of a 80:20 mixture of diastereomers after recrystallization from methanol/water. Recrystallization from dimethylformamide/water gave a 60:40 mixture of diastereomers, m.p. 225°–235° C.

| ANALYSIS: | | | |
|---|---|---|---|
| Calculated for $C_{20}H_{18}N_2O$: | 79.44% C | 6.00% H | 9.27% N |
| Found: | 79.37% C | 5.98% H | 9.26% N |

EXAMPLE 4

2-(4-Fluorophenyl)-1,2,3a,4,5,6-hexahydro[1,3]oxazino[6,5,4-kl]acridine

A mixture of 9-amino-1,2,3,4-tetrahydroacridin-1-ol (7.77 g), 4-fluorobenzaldehyde (5.9 g) and morpholine (6.3 ml) in 400 ml of xylenes was refluxed with removal of water for sixteen hours.

The solvent was then removed and the desired compound was purified via flash chromatography (20% isopropanol/ethyl acetate) to give 3.5 g of a yellow solid, m.p. 220°–234° C. (dec.). This was recrystallized from methanol/water to give 2.3 g of a yellow solid, m.p. 238°–241° C. (dec.).

ANALYSIS:

| | | | |
|---|---|---|---|
| Calculated for $C_{20}H_{17}FN_2O$: | 74.98% C | 5.35% H | 8.74% N |
| Found: | 74.93% C | 5.47% H | 8.71% N |

We claim:

1. A compound of the formula

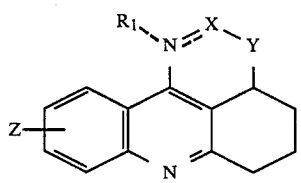

where
R$_1$ is hydrogen, loweralkyl or aryloweralkyl;
Z is hydrogen, loweralkyl, loweralkoxy, hydroxy, nitro or trifluoromethyl;
Y is O or NR$_2$, R$_2$ being hydrogen, loweralkyl or aryloweralkyl; and
X is CR$_3$, CHR$_3$, C=O, C=S or CHN(CH$_3$)$_2$, R$_3$ being hydrogen, loweralkyl or aryl;
or a stereo isomer thereof or a pharmaceutically acceptable acid addition salt thereof.

2. The compound as defined in claim 1, where Z is hydrogen.

3. The compound as defined in claim 1, where X is CR$_3$ or CHR$_3$.

4. The compound as defined in claim 2, where X is CR$_3$ or CHR$_3$.

5. The compound as defined in claim 1, which is 3a,4,5,6-tetrahydro-2-methyl-(3H)-pyrimidino[4,5,6-kl]acridine.

6. The compound as defined in claim 1, which is 3a,4,5,6-tetrahydro-2-phenyl-(3H)-pyrimidino[4,5,6-kl]acridine.

7. The compound as defined in claim 1, which is 2-phenyl-1,2,3a,4,5,6-hexahydro[1,3]oxazino[6,5,4-kl]acridine.

8. The compound as defined in claim 1, which is 2-(4-fluorophenyl)-1,2,3a,4,5,6-hexahydro[1,3]oxazino[6,5,4-kl]acridine.

9. A pharmaceutical composition comprising a compound as defined in claim 1 in an amount sufficient to alleviate a memory dysfunction characterized by cholinergic deficit, and a suitable carrier therefor.

10. A pharmaceutical composition comprising a compound as defined in claim 2 in an amount sufficient to alleviate a memory dysfunction characterized by cholinergic deficit, and a suitable carrier therefor.

11. A pharmaceutical composition comprising a compound as defined in claim 3 in an amount sufficient to alleviate a memory dysfunction characterized by cholinergic deficit, and a suitable carrier therefor.

12. A pharmaceutical composition comprising a compound as defined in claim 4 in an amount sufficient to alleviate a memory dysfunction characterized by cholinergic deficit, and a suitable carrier therefor.

13. A method of treating a patient in need of relief from memory dysfunction characterized by cholinergic dysfunction which comprises administering to the patient an effective amount of a compound as defined in claim 1.

* * * * *